United States Patent

Mewshaw et al.

[11] Patent Number: 6,103,744
[45] Date of Patent: Aug. 15, 2000

[54] 4-AMINOALKOXY-1,3-DIHYDROBENZOIMIDAZOL-2-ONE DOPAMINE AUTORECEPTOR AGONISTS

[75] Inventors: Richard Eric Mewshaw, Princeton, N.J.; James Albert Nelson, Washington Crossing, Pa.; Uresh Shantilal Shah, Cranbury, N.J.

[73] Assignee: American Home Products Corporation, Madison, N.J.

[21] Appl. No.: 09/394,448

[22] Filed: Sep. 10, 1999

Related U.S. Application Data

[62] Division of application No. 09/025,083, Feb. 17, 1998, Pat. No. 5,990,144.
[60] Provisional application No. 60/038,682, Feb. 18, 1997.
[51] Int. Cl.[7] .......................... A61K 31/415; A61K 31/34; A61K 31/38; A61K 31/44
[52] U.S. Cl. .......................... 514/387; 514/387; 514/468; 514/397; 514/402; 514/406; 514/438; 514/443; 514/305
[58] Field of Search .......................... 514/385, 387, 514/468, 397, 402, 406, 438, 443, 305, 756

[56] References Cited

U.S. PATENT DOCUMENTS 5,750,556  5/1998  Mewshaw et al. .................. 514/411
5,990,144  11/1999  Mewshaw et al. .................. 514/387

*Primary Examiner*—Theodore J. Criares
*Attorney, Agent, or Firm*—Rebecca R. Barrett

[57] ABSTRACT

Disclosed are compounds of the formula

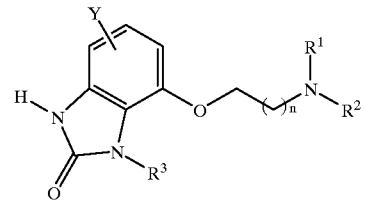

wherein:

$R^1$ is hydrogen or $C_1-C_6$ alkyl;

$R^2$ is selected from hydrogen, straight-chain and branched $C_1-C_{10}$ alkyl, cyclohexylmethyl or $-(CH_2)_m Ar$ where Ar is phenyl, naphthyl, thienyl, furanyl or pyridinyl, each optionally substituted by one or two substituents selected independently from $C_1-C_6$ alkyl, halogen, $C_1-C_6$ alkoxide and trifluoromethyl;

or $NR^1R^2$ is 1, 2, 3, 4-tetrahydroquinolin-1-yl or 1, 2, 3, 4-tetrahydroisoquinolin-2-yl;

m is 1–5;

n is 1 or 2;

$R^3$ is hydrogen or $C_1-C_6$ alkyl;

Y is halogen, $C_1-C_6$ alkyl, and $C_1-C_6$ alkoxy;

or a pharmaceutically acceptable salt thereof, which are dopamine autoreceptor agonists and as such are useful in the treatment of schizophrenia, Parkinson's disease, Tourette's syndrome, alcohol addiction and drug addiction.

5 Claims, No Drawings

4-AMINOALKOXY-1,3-DIHYDROBENZOIMIDAZOL-2-ONE DOPAMINE AUTORECEPTOR AGONISTS

This application is a divisional application of U.S. Ser. No. 09/025,083, filed Feb. 17, 1998, U.S. Pat. No. 5,990,144 (not yet known) which claims the benefit of prior U.S. Provisional application No. 60/038,682 filed Feb. 18, 1997.

FIELD OF INVENTION

This invention relates to a series of 4-aminoalkoxy-1,3-dihydrobenzoimidazol-2-ones having dopaminergic properties and thus have utility in treating Parkinson's disease, Tourette's syndrome, schizophrenia, and alcohol and drug addiction.

BACKGROUND OF THE INVENTION

The compounds of this invention are dopamine agonists having various degrees of intrinsic activity and are essentially free from extrapyramidal side effects. Some of the compounds are selective autoreceptor agonists, and therefore partial agonists (i.e. activate only autoreceptors versus postsynaptic $D_2$ dopamine receptors). Efforts to induce antipsychotic activity with dopamine autoreceptor agonists have been successful (Dorsini et al., Adv. Biochem. Psychopharmacol., 16, 645–648, 1977; Tamminga et al., Science, 200, 567–568; and Tamminga et al., Psychiatry, 398–402, 1986).

As selective autoreceptor agonists, the invention compounds provide functional modulation of the dopamine systems of the brain without the excessive blockade of the postsynaptic dopamine receptors which have been observed to be responsible for the serious side effects frequently exhibited by agents found otherwise clinically effective for the treatment of schizophrenia Activation of the dopamine autoreceptors results in reduced neuronal firing a well as inhibition of dopamine synthesis and release and therefore provides a means of controlling hyperactivity of the dopaminergic systems.

The compounds of this invention were also found to have high intrinsic activity and therefore they can behave as the natural neurotransmitter, i.e., as full agonists. As such, they are useful in the treatment of diseases having abnormal concentrations of dopamine could be used as dopamine surrogates such as schizophrenia, Parkinson's disease and Tourette's syndrome. Such agents are partial agonists at the postsynaptic dopamine $D_2$ receptor and are thereby useful in the treatment of alcohol and drug addiction.

In the Belgian patent 850,166, Ciba-Geigy discloses compounds represented by the compound of the formula below which have both a and P-adrenergic properties and are useful as cardiovascular and antihypertensive agents.

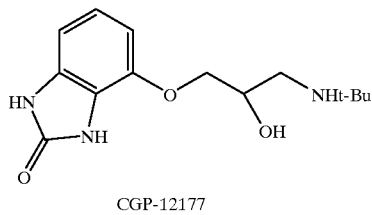

CGP-12177

SUMMARY OF THE INVENTION

Compounds of this invention are 4-aminoalkoxy-1,3-dihydro-benzoimidazol-2-ones which are illustrated by Formula I below

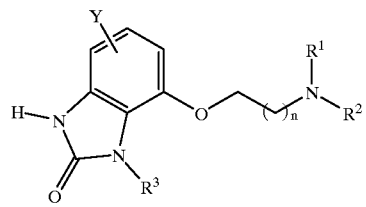

wherein:

$R^1$ is hydrogen or $C_1$–$C_6$ alkyl;

$R^2$ is selected from hydrogen, straight-chain and branched $C_1$–$C_{10}$ alkyl, cyclohexylmethyl or —$(CH_2)_m$Ar where Ar is phenyl, naphthyl, thienyl, furanyl or pyridinyl, each optionally substituted by one or two substituents selected independently from $C_1$–$C_6$ alkyl, halogen, $C_1$–$C_6$ alkoxide and trifluoromethyl;

or $NR^1R^2$ is 1, 2, 3, 4-tetrahydroquinolin-1-yl or 1, 2, 3, 4-tetrahydroisoquinolin-2-yl;

m is 1–5;

n is 1 or 2;

$R^3$ is hydrogen or $C_1$–$C_6$ alkyl;

Y is halogen, $C_1$–$C_6$ alkyl, and $C_1$–$C_6$ alkoxy;

and the pharmaceutically acceptable salts thereof.

Acid addition salts can be formed with an invention compound and a pharmaceutically acceptable acid including, but not limited to, the hydrochloride, hydrobromide, hydroiodide, sulfate, phosphate, nitrate, acetate, fumarate, succinate, citrate, maleate, lactate, and benzoate salts.

The compounds of this invention are dopamine autoreceptor agonists, that is, they serve to modulate the synthesis and release of the neurotranmitter dopamine. They are thus useful for treatment of disorders of the dopaminergic system, such as schizophrenia, Parkinson's disease and Tourette's syndrome. Such agents are partial agonists at the postsynaptic dopamine $D_2$ receptor and are thereby useful in the treatment of alcohol and drug addiction.

DETAILED DESCRIPTION OF THE INVENTION

The compounds of Formula I are generally prepared by the overall sequence depicted in Schemes I–IV. When one or both of $R^1$ and $R^2$ is hydrogen, it is desirable to protect the basic nitrogen with a suitable protecting group such as the trifluoroacetyl group or t-butyloxycarbonyl group. Scheme I outlines a procedure to prepare an invention compound where $R^2$ and $R^3$ are H.

Scheme I

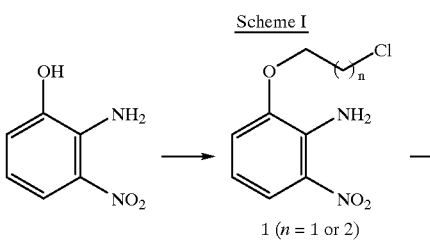

1 (n = 1 or 2)

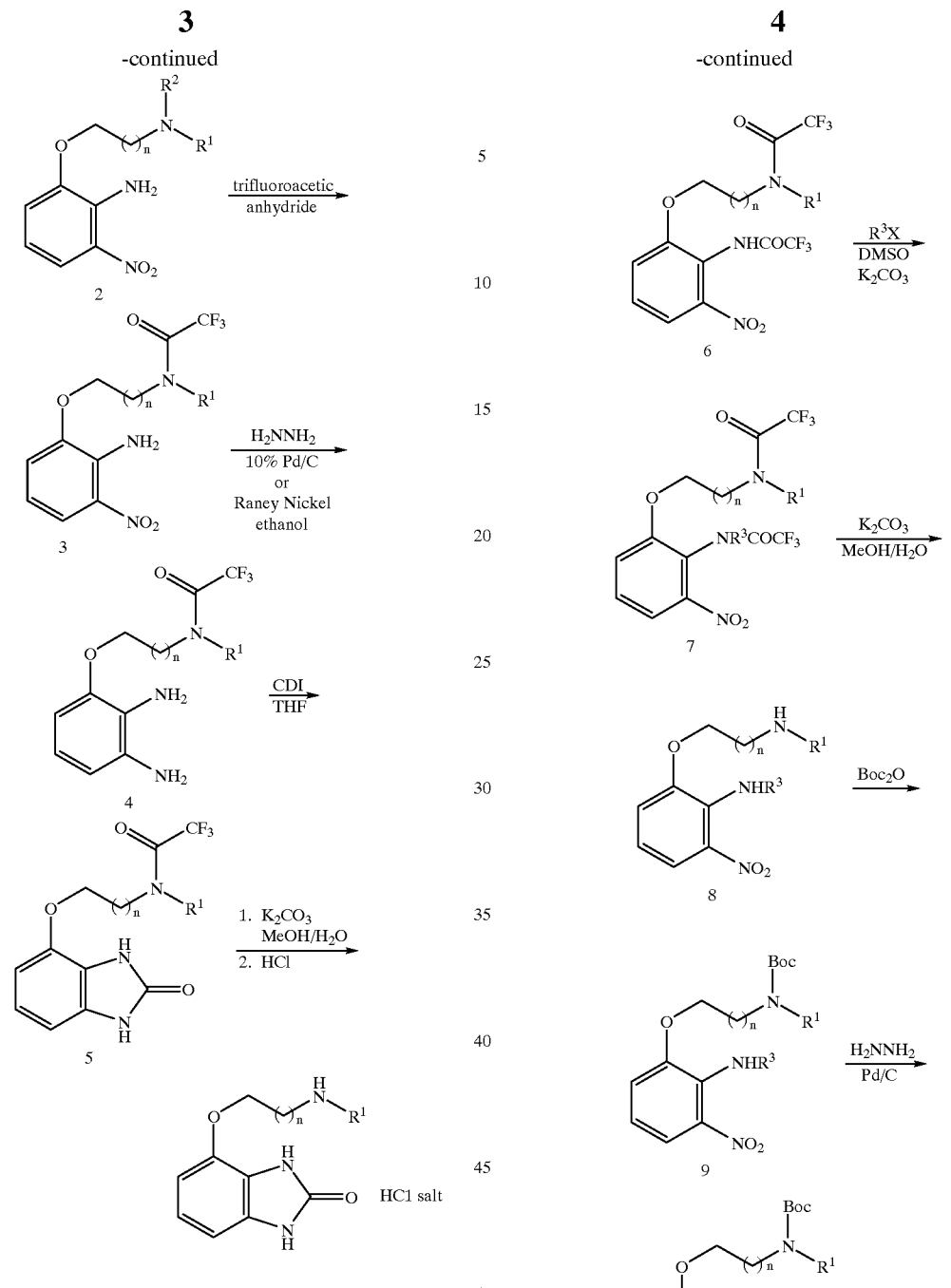
Scheme II shows a synthetic route for invention compounds where $R^3$ is not H.
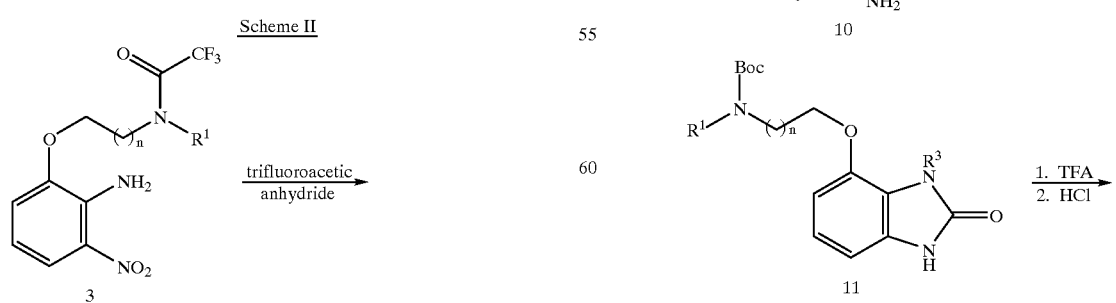

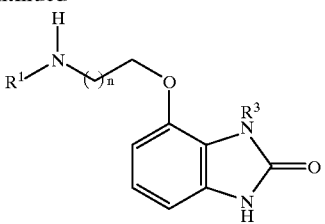

Scheme III shows a synthetic route for invention compounds where neither of $R^1$ and $R^2$ is H.

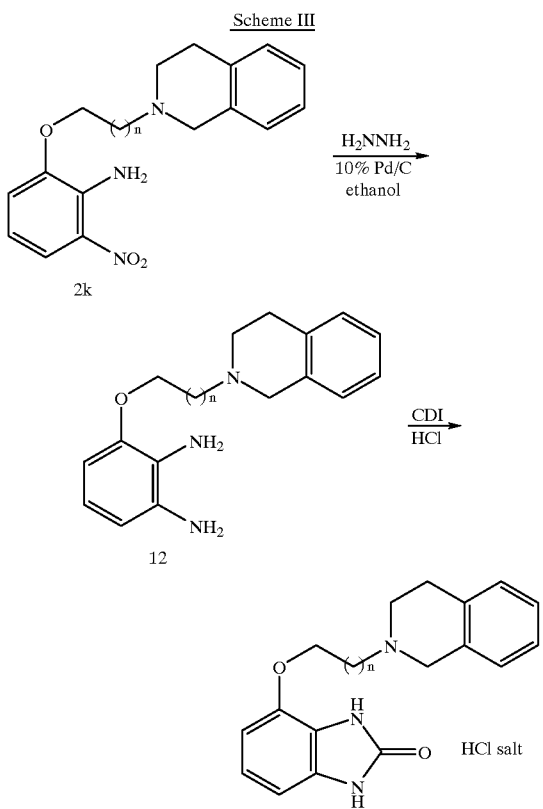

Scheme IV shows the procedure used to prepare an intermediate where Y is Cl.

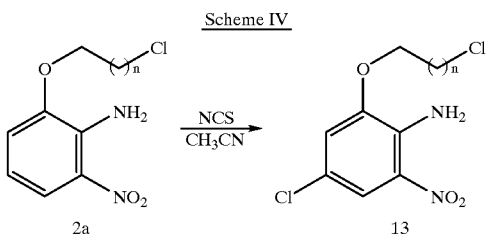

The following specific examples illustrate the synthetic procedures for the preparation of intermediates and invention compounds and should not be construed as limiting the scope of this disclosure. Those skilled in the art of organic synthesis may be aware of still other routes to prepare invention compounds. Reactants and intermediates are either commercially available or can be prepared according to standard literature procedures.

Intermediate 1a 2-(2-Chloro-ethoxy)-6-nitro-phenylamine

Method 1.

To a solution of 2-amino-3-nitrophenol (5.0 g, 32.4 mmol), triphenylphosphine (12.8 g, 48.7 mmol) and 2-chloroethanol (3.9 g, 48.7 mmol) in tetrahydrofuran (120 mL) at 0–5° C. was added over 30 min a solution of diethyl azodicarboxylate (8.5 g, 48.7 mmol) in tetrahydrofuran (75 mL). The mixture was warmed to 23° C. and stirred for 18 hr. The solvent was removed under vacuum to give a dark brown oil. Purification by chromatography (1.3 kg silica gel, 30% hexane—ethyl acetate) afforded 3.1 g (44.2%) of an orange solid, mp 71–73° C.; MS (+)PBEI m/e 216/218 (M$^+$).

Elemental analysis for $C_8H_9ClN_2O_3$: Calc'd: C, 44.36; H, 4.19; N, 12.93. Found: C, 44.45; H, 4.02; N, 12.97.

Method 2.

A slurry containing 2-amino-3-nitrophenol (32.0 g, 0.208 mol), 1,2-dichloroethane (260.0 g, 2.65 mol), potassium carbonate (35.0 g, 0.252 mol) and 2-butanone (750 mL) was refluxed for 24 hr. The mixture was cooled, filtered and the solids were washed with ethyl acetate. The filtrate was concentrated to an oily residue that was dissolved in ethyl acetate (500 mL). The organic layer was washed with 1 N sodium hydroxide (250 mL), water (500 mL), and brine (2×500 mL), dried over anhydrous magnesium sulfate. Concentration of the filtered solution and trituration of the residue with hexane afforded 37.8 g (84.6%) of product as an orange solid, mp 71–73° C.; MS (+)PBEI m/e 216/218 (M$^+$)

Intermediate 1b 2-(3-Bromo-propoxy)-6-nitro-phenylamine

Following the procedure of method 2 above, and using 1,3-dibromopropane, the tide compound was as a yellow solid, (78.7%) mp 88–89° C.; MS EI m/e 274/276 (M$^+$).

Elemental analysis for $C_9H_{11}BrN_2O_3$: Calc'd: C, 39.29; H. 4.03; N, 10.18. Found: C, 39.71; H, 3.91; N, 10.27.

Intermediate 2a 2-(2-Benzylamino-ethoxy)-6-nitro-phenylamine

A mixture of 2-(2-chloro-ethoxy)-6nitro-phenylamine (1a, 3.0 g, 13.8 mmol) and benzylamine (9.0 g, 84.0 mmol) was heated neat at 100–110° C. for 6 hr. The excess benzylamine was removed by distillation under vacuum (70–75° C./0.1 mm). The residue was poured into 1 N sodium hydroxide (300 mL) and extracted with ethyl acetate (2×, 300 mL). The combined organic layer was washed with water (2×, 300 mL) and brine (300 mL). The ethyl acetate layer was dried over anhydrous magnesium sulfate, filtered, and the solvent removed under vacuum to give 5.1 g of crude red oil. Purification by chromatography (500 g silica gel, ethyl acetate: 2 M $NH_3$ in methanol, 20:1) afforded 3.54 g (89.3%) of a red semi-solid, mp 33–60° C.; MS EI m/e 287 (M$^+$).

Elemental analysis for $C_{15}H_{17}N_3O_3$: Calc'd: C, 62.71; H, 5.96; N, 14.62. Found: C, 62.64; H, 6.04; N, 14.23.

[1]DMSO can be used as a solvent in this reaction.

Using this general procedure and utilizing 2-(2-chloro-ethoxy)-6-nitro-phenylamine or 2-(3-bromo-propoxy)-6-nitro-phenylamine or 4-chloro-2-(2-chloro-ethoxy)-6-nitro-phenylamine and 4methyl-benzylamine, 1-naphthalene-methylamine, 4-tert-butyl-benzylamine, thiophene-2-methyl-amine, 4-chloro-benzylamine, thiophene-3-methylamine, 1,2,3,4-tetrahydroisoquinoline or 3-phenyl-1-propylamine produced the following intermediates 2b–2l, respectively:

2b 2-[2-(4-Methyl-benzylamino)-ethoxy]-6-nitro-phenylamine as a yellow solid (89%), mp 55–57° C.; EI m/e 301 (M$^+$).

Elemental analysis for $C_{16}H_{19}N_3O_3$: Calc'd: C, 62.71; H, 5.96; N, 14.62. Found: C, 62.64; H, 6.04; N, 14.23.

2c 2-(3-Benzylamino-propoxy)-6-nitro-phenylamine as a viscous orange oil (85.5%); MS EI m/e 301 (M$^+$).

Elemental analysis for $C_{16}H_{19}N_3O_3$: Calc'd: C, 63.77; H, 6.36; N, 13.94. Found: C, 63.66; H, 6.28; N, 13.89.

2d 2-{2-[(Naphthalen-1-ylmethyl)-amino]-ethoxy}-6-nitro-phenylamine as a yellow solid (76.3%), mp 66–67° C.; MS EI m/e 337 (M$^+$).

Elemental analysis for $C_{19}H_{19}N_3O_3$: Calc'd: C, 67.64; H, 5.68; N, 12.45. Found: C, 67.20; H, 5.66; N, 12.26.

2e 2-[2-(4-tert-Butylbenzylamino)-ethoxy]-6-nitro-phenylamine as an orange viscous oil (83.3%); MS EI m/e 343 (M$^+$).

Elemental analysis for $C_{19}H_{25}N_3O_3 \cdot 0.25\ H_2O$: Calc'd: C, 65.59; H, 7.39; N, 12.07. Found: C, 65.89; H, 7.20; N, 11.94.

2f 2-Nitro-6-{2-[(thiophen-2-ylmethyl)-amino]-ethoxy}-phenylamine as a red semi-solid material (88.5%); MS EI m/e 389 (M$^+$).

Elemental analysis for $C_{13}H_{15}N_3O_3S$: Calc'd: C, 53.23; H, 5.15; N, 14.32. Found: C, 52.86; H, 4.93; N, 14.15.

2 g 2-[2-(4-Chloro-benzylamino)-ethoxy]-6-nitro-phenylamine as an orange solid (87.8%), mp 61–62° C.; MS EI m/e 322/324 (M$^+$).

Elemental analysis for $C_{15}H_{16}N_3O_3 \cdot 0.25\ H_2O$: Calc'd: C, 55.22; H, 5.10; N, 12.88. Found: C, 55.27; H, 4.96; N, 12.88.

2h 2-(2-Benzylamino-ethoxy)-4-chloro-6-nitro-phenylamine as a orange-brown colored solid (54.0%), mp 87–88° C.; MS EI m/e 321/323 (M$^+$).

Elemental analysis for $C_{15}H_{16}ClN_3O_3$: Calc'd: C, 55.99; H, 5.01; N, 13.06. Found: C, 55.85; H, 4.90; N, 13.13.

2i 4-Chloro-2-nitro-6-{2-[(thiophen-2-ylmethyl)-amino]-ethoxy}-phenylamine as a yellow solid (44.0%), mp 74–75° C.; MS EI m/e 327/329 (M$^+$).

Elemental analysis for $C_{13}H_{14}ClN_3O_2S$: Calc'd: C, 47.67; H, 4.33; N, 12.75. Found: C, 47.54; H, 4.11; N, 13.06.

2j 4-Chloro-2-nitro-6-{2-[(thiophen-3-ylmethyl)-amino]-ethoxy}-phenylamine as a yellow solid (33.3%), mp 77–78° C.; MS EI m/e 327/329 (+).

Elemental analysis for $C_{13}H_{14}ClN_3O_2S$: Calc'd: C, 47.67; H, 4.33; N, 12.75. Found: C, 47.54; H, 4.18; N, 12.80.

2k 2-[2-(3,4-Dihydro-1H-isoquinolin-2-yl)-ethoxy]-6-nitro-phenylamine as a yellow solid (87.1%), mp 95–97° C.; MS EI m/e 313 (M$^+$).

Elemental analysis for $C_{17}H_{19}N_3O_2$: Calc'd: C, 65.16; H, 6.11; N, 13.41. Found: C, 64.87; H, 6.11; N, 13.40.

2l 2-Nitro-6-[2-(-phenyl-propylamino)-ethoxy]-phenylamine as a viscous orange oil (83.9%); MS EI m/e 315 (M$^+$).

Elemental analysis for $C_{17}H_{21}N_3O_3 \cdot 0.25\ H_2O$: Calc'd: C, 63.83; H, 6.77; N, 13.14. Found: C, 63.90; H, 6.56; N, 13.07.

Intermediate 3a

N-[2-(2-Amino-3-nitro-phenoxy)-ethyl]-N-benzyl-2,2,2-trifluoro-acetamide

To a solution of 2-(2-benzylamino-ethoxy)-6-nitro-phenylamine (2a, 0.5 g, 1.74 mmol) and triethylamine (0.32 mL, 3.48 mmol) in anhydrous methylene chloride (10 mL) at 23° C. was added trifluoroacetic anhydride (0.32 mL, 2.26 mmol). After 2 hr the reaction was diluted with ether and washed with saturated sodium bicarbonate (3×80 mL) and the organic layer dried over anhydrous magnesium sulfate. Filtration and evaporation of the solvent gave 0.55 g (81.7%) of yellow solid, mp 134–135° C.; MS EI m/e 383 (M$^+$).

Elemental analysis for $C_{17}H_{16}F_3N_3O_4$: Calc'd: C, 53.27; H, 4.21; N, 10.96. Found: C, 53.09; H, 4.35; N, 10.93.

Following this general procedure and using 2-[2-(4-methyl-benzylamino)-ethoxy]-6-nitro-phenylamine, 2-(3-benzylamino-propoxy)-6-nitro-phenylamine, 2-{2-[(naphthalen-1-ylmethyl)-amino]-ethoxy}-6-nitro-phenylamine, 2-[2-(4-tert-butylbenzylamino)-ethoxy]-6nitro-phenyl-amine, 2-nitro-6-{2-[(thiophen-2-ylmethyl)-amino]-ethoxy}-phenylamine, 2-[2-(4-chloro-benzylamino)-ethoxyl-6-nitro-phenylamine, 2-(2-benzylamino-ethoxy)4-chloro-6-nitro-phenylamine, 4-chloro-2-nitro-6-{2-[(thiophen-2-ylmethyl)-amino]-ethoxy}-phenylamine, 4chloro-2-nitro-6-{2-[(thiophen-3-ylmethyl)-amino]-ethoxy}-phenylamine and 2-nitro-6-[2-(3-phenyl-propylamino)-ethoxy]-phenylamine gave respectively:

3b N-[2-(2-Amino-3-nitro-phenoxy)-ethyl]-2,2,2-trifluoro-N-(4-methyl-benzyl) acetamide as a yellow solid (79%), mp 172–173° C.; MS EI m/e 397 (M$^+$).

Elemental analysis for $C_{18}H_{18}F_3N_3O_4$: Calc'd: C, 54.41; H, 4.57; N, 10.58. Found: C, 54.34; H, 4.33; N, 10.53.

3c N-[3-(2-Amino-3-nitro-phenoxy)-propyl]-N-benzyl-2,2,2-trifluoro-acetamide as a yellow solid (67.8%), mp 92–93° C.; MS EI m/e 397 (M$^+$).

Elemental analysis for $C_{18}H_{18}F_3N_3O_4$: Calc'd: C, 54.41; H, 4.57; N, 10.58. Found: C, 54.30; H, 4.50; N, 10.50.

3d N-[2-(2-Amino-3-nitro-phenoxy)-ethyl]-2,2,2-trifluoro-N-naphthalen-1-ylmethyl-acetamide as a yellow-orange colored solid (75.3%), mp 133–135° C.; MS EI m/e 433 (M$^+$).

Elemental analysis for $C_{21}H_{18}F_3N_3O_4$: Calc'd: C, 58.20; H, 4.19; N, 9.70. Found: C, 58.28; H, 4.07; N, 9.48.

2e N-[2-(2-Amino-3-nitro-phenoxy)-ethyl]-N-(4-tert-butyl-benzyl)-2,2,2-trifluoro-acetamide as a yellow solid (82.0%), mp 80–82° C.; MS EI m/e 439 (M$^+$).

Elemental analysis for $C_{21}H_{24}F_3N_3O_4$: Calc'd: C, 57.40; H, 5.51; N, 9.56. Found: C, 57.09; H, 5.31; N, 9.40.

3f N-[2-(2-Amino-3-nitro-phenoxy)-ethyl]-2,2,2-trifluoro-N-thiophen-2-ylmethyl-acetamide as a yellow solid (77.4%) mp 143–144° C.; MS EI m/e 389 (M$^+$).

Elemental analysis for $C_{15}H_{14}F_3N_3O_4S$: Calc'd: C, 46.27; H, 3.62; N, 10.79. Found: C, 46.19; H, 3.39; N, 10.64.

3 g N-[2-(2-Amino-3-nitro-phenoxy)-ethyl]-N-(4-chloro-benzyl)-2,2,2-trifluoro-acetamide as a yellow solid (84.0%), mp 138–139° C.; MS (+)FAB m/e 418/420 (M+H$^{30}$ )

Elemental analysis for $C_{17}H_{15}ClF_3N_3O_4$: Calc'd: C, 48.88; H, 3.62; N, 10.06. Found: C, 48.66; H, 3.47; N, 9.82.

3h N-[2-(2-Amino-5-chloro-3-nitro-phenoxy)-ethyl]-N-benzyl-2,2,2-trifluoro-acetamide as a yellow solid (67.9%), mp 106–108° C.; MS (+)FAB, m/e 418/420 (M+H$^+$).

Elemental analysis for $C_{17}H_{15}ClF_3N_3O_4$: Calc'd: C, 48.88; H, 3.62; N, 10.06. Found: C, 48.96; H, 3.50; N, 10.03.

3i N-[2-(2-Amino-5-chloro-3-nitro-phenoxy)-ethyl]-2,2,2-trifluoro-N-thiophen-2-ylmethyl-acetamide as a yellow solid (59.6%), mp 97–98° C.; MS EI m/e 423/425 (M$^+$).

Elemental analysis for $C_{15}H_{13}ClF_3N_3O_4S$: Calc'd: C, 42.51; H, 3.09; N, 9.92. Found: C, 42.37; H, 2.97; N, 9.84.

3j N-[2-(2-Amino-5-chloro-3-nitro-phenoxy)-ethyl]-2,2,2-trifluoro-N-thiophen-3-ylmethyl-acetamide as a yellow solid (80.0%), mp 149–150° C.; MS EI m/e 423/425 (M$^+$).

Elemental analysis for $C_{15}H_{13}ClF_3N_3O_4S$: Calc'd: C, 42.51; H, 3.09; N, 9.92. Found: C, 42.02; H, 2.95; N, 9.78.

3k N-[2-(2-amino-3-nitro-phenoxy)-ethyl]-2,2,2-trifluoro-N-(3-phenyl-propyl)-acetamide as a yellow solid (72.6%), mp 81–82° C.; MS EI m/e 411 (M$^+$).

Elemental analysis for $C_{19}H_{20}F_3N_3O_4$: Calc'd: C, 55.47; H, 4.90; N, 10.21. Found: C, 55.57; H, 4.66; N, 10.23.

Intermediate 4a

N-Benzyl-N-[2-(2,3-diamino-phenoxy)-ethyl]-2,2,2-trifluoro-acetamide

To a mixture of N-[2-(2-ano-3-nitro-phenoxy)-ethyl]-N-benzyl-2,2,2-trifluoro-acetamide (3a, 2.4 g, 6.26 mmol) and 10% palladium on carbon (0.40 g) in ethanol (200 mL) at 50–55° C. was added a solution of hydrate hydrate (2.0 g) in ethanol (25 mL). The reaction was allowed to stir for 18 hr at 23° C., then the catalyst filtered through solka floc and the solvent removed under vacuum to afford 1.96 g (88.9%) of an amber-colored oil. Crystallization from ethyl acetate—hexane gave a white solid, mp 118–119° C.; MS (+)FAB m/e 354 (M+H$^+$).

Elemental analysis for $C_{17}H_{18}F_3N_3O_2$: Calc'd: C, 56.58; H, 4.72; N, 12.38. Found: C, 57.49; H, 5.10; N, 11.86. Following the above procedure and utilizing N-[2-(2-amino-3-nitro-phenoxy)-ethyl]-2,2,2-trifluoro-N-(4-methyl-benzyl) acetamide, N-[3-(2-amino-3-nitro-phenoxy)-propyl]-N-benzyl- 2,2,2-trifluoro-acetamide, N-[2-(2-amino-3-nitro-phenoxy)-ethyl]-2,2,2-trifluoro-N-naphthalen-1-ylmethyl-acetamide, N-[2-(2-amino-3-nitro-phenoxy)-ethyl]-N-(4-tert-butyl-benzyl)-2,2,2-trifluoro-acetamide, N-[2-(2-amino-3-nitro-phenoxy)-ethyl]-2,2,2-trifluoro-N-thiophen-2-ylmethyl-acetamide, N-[2-(2-amino-3-nitro-phenoxy)-ethyl]-N-(4-chlorobenzyl)-2,2,2-trifluoro-acetamide, N-[2-(2-ano-5-chloro-3-nitro-phenoxy)-ethyl]-N-benzyl-2,2,2-trifluoro-acetamide, N-[2-(2-amino-5-chloro-3-nitro-phenoxy)-ethyl]-2,2,2-trifluoro-N-thiophen-2-ylmethyl-acetamide, and N-[2-(2-amino-5-chloro-3-nitro-phenoxy)-ethyl]-2,2,2-trifluoro-N-thiophen-3-ylmethyl-acetamide afforded respectively:

4b N-[2-(2,3-Diamino-phenoxy)-ethyl]-2,2,2-trifluoro-N-(4-methyl-benzyl)-acetamide as a white solid (85.0%), mp 94–96° C.; MS EI m/e 367 (M$^+$).

Elemental analysis for $C_{18}H_{20}F_3N_3O_2$: Calc'd: C, 58.85; H, 5.49; N, 11.44. Found: C, 58.91; H, 5.32; N, 11.45.

4c N-Benzyl-N-[3-(2,3-diamino-phenoxy)-propyl]-2,2,2-trifluoro-acetamide as a white solid (86.5%), mp 56–58° C.; MS EI m/e 367 (M$^+$).

Elemental analysis for $C_{18}H_{20}F_3N_3O_2$: Calc'd: C, 58.85; H, 5.49; N, 11.44. Found: C, 59.00; H, 5.42; N, 11.48.

4d N-[2-(2,3-Diamino-phenoxy)-ethyl]-2,2,2-trifluoro-N-naphthalen-1-ylmethyl-acetamide as a viscous yellow oil (63.0%); MS (+)FAB m/e 404 (M+H$^+$).

Elemental analysis for $C_{21}H_{20}F_3N_3O_2$: Calc'd: C, 62.53; H, 5.00; N, 10.42. Found: C, 62.45; H, 4.98; N, 10.20.

4e N-(4-tert-Butyl-benzyl)-N-[2-(2,3-diamino-phenoxy)-ethyl]-2,2,2-trifluoro-acetamide as a viscous brown oil (72.7%); MS EI m/e 409 (M$^+$).

4f N-[2-(2,3-Diamino-phenoxy)-ethyl]-2,2,2-trifluoro-N-thiophen-2-ylmethyl-acetamide as a white solid (41.0%), mp 72–74° C.; MS (+)FAB m/e 404 (M+H$^+$).

Elemental analysis for $C_{15}H_{16}F_3N_3O_2S$: Calc'd: C, 50.13; H, 4.49; N, 11.69. Found: C, 50.09; H, 4.38; N, 11.59.

4 g N-(4-Chloro-benzyl)-N-[2-(2,3-diamino-phenoxy)-ethyl]-2,2,2-trifluoro-acetamide as a brown oil (80.9%); MS EI m/e 387/389 (M$^+$).

Elemental analysis for $C_{17}H_{17}ClF_3N_3O_2$: Calc'd: C, 52.65; H, 4.42; N, 10.84. Found: C, 52.47; H, 4.51; N, 10.60.

4h N-Benzyl-N-[2-(2,3-diamino-5-chloro-phenoxy)-ethyl]-2,2,2-trifluoro-acetamide as a viscous brown oil (76.2%); MS EI m/e 387/389 (M$^+$).

Elemental analysis for $C_{17}H_{17}ClF_3N_3O_2$: Calc'd: C, 52.65; H, 4.42; N, 10.84. Found: C, 52.47; H, 4.39; N, 10.90.

4i N-[2-(2,3-Diamino-5-chloro-phenoxy)-ethyl]-2,2,2-trifluoro-N-thiophen-2-ylmethyl-acetamide as a viscous brown oil (71.4%); MS EI m/e 393/395 (M$^+$).

Elemental analysis for $C_{15}H_{15}ClF_3N_3O_2S$: Calc'd: C, 45.75; H, 3.84; N, 10.67. Found: C, 45.58; H, 3.93; N, 10.64.

4i N-[2-(2,3-Diamino-5-chloro-phenoxy)-ethyl]-2,2,2-trifluoro-N-thiophen-3-ylmethyl-acetamide as a viscous brown oil (75.0%); MS EI m/e 393/395 (M$^+$).

Elemental analysis for $C_{15}H_{15}ClF_3N_3O_2S$: Calc'd: C, 45.75; H, 3.84; N, 10.67. Found: C, 45.39; H, 3.84; N, 10.56.

Intermediate 5a

N-Benzyl-2,2,2-trifluoro-N-[2.(2-oxo-2,3-dihydro-1H-benzoimidazol-4-yloxy)-ethyl]-acetamide A mixture of N-benzyl-N-[2-(2,3-diamino-phenoxy)-ethyl]-2,2,2-trifluoro-acetamide (0.28 g, 0.804 mmol) and diimidazole carbonyl (0.326 g, 2.0 mmol) in anhydrous tetrahydrofuran (10 mL) was stirred at 23° C. for 2 hr. The reaction was poured into water and extracted with ethyl acetate (2×150 mL). The organic layer dried over anhydrous magnesium sulfate, filtered, and the solvent removed under vacuum. Purification by chromatography (60 g silica gel, ethyl acetate: hexane: 2 M NH$_3$ in methanol (15:5:1)) afforded 0.29 g (94.8%) of a colorless oil. Crystallization from hexane gave a white solid, mp 121–123° C.; MS EI m/e 379 (M$^+$).

Elemental analysis for $C_{18}H_{16}F_3N_3O_3$: Calc'd: C, 56.99; H, 4.25; N, 11.08. Found: C, 57.09; H, 4.07; N, 11.10.

Utilizing N-[2-(2,3-diamino-phenoxy)-ethyl]-2,2,2-trifluoro-N-(4-methyl-benzyl)-acetamide, N-benzyl-N-[3-(2,3-diamino-phenoxy)-propyl]-2,2,2-trifluoro-acetamide, N-[2-(2,3 diamino-phenoxy)-ethyl]-2,2,2-trifluoro-N-naphthalen-1-ylmethyl-acetamide, N-(4-tert-butyl-benzyl)-N-[2-(2,3-diamino-phenoxy)-ethyl]-2,2,2-trifluoro-acetamide, N-[2-(2,3-diamino-phenoxy)-ethyl]-2,2,2-trifluoro-N-thiophen-2-ylmethyl-acetamide, N-(4-chloro-benzyl)-N-[2-(2,3-diamino-phenoxy)-ethyl]-2,2,2-trifluoro-acetamide, N-benzyl-N-[2-(2,3-diamino-5-chloro-phenoxy)-ethyl]-2,2,2-trifluoro-acetamide, N-[2-(2,3-diamino-5-chloro-phenoxy)-ethyl]-2,2,2-trifluoro-N-thiophen-2-ylmethyl-acetamide and N-2-(2,3-diamino-5-chloro-phenoxy)-ethyl]-2,2,2-trifluoro-N-thiophen-3-ylmethyl-acetamide in the above general procedure afforded respectively:

5b 2,2,2-Trifluoro-N-(4-methyl-benzyl)-N-[2-(2-oxo-2,3-dihydro-1H-benzoimidazol-4-yloxy)-ethyl]-acetamide·0.1 ethyl acetate as a white solid (96.6%), mp 194–196° C.; MS (+)FAB m/e 394 (M+H$^+$).

Elemental analysis for $C_{19}H_{18}F_3N_3O_3$·0.1 $C_4H_8O_2$ Calc'd: C, 57.94; H, 4.71; N, 10.45. Found: C, 57.90; H, 4.60; N, 10.19.

5c N-Benzyl-2,2,2-trifluoro-N-[3-(2-oxo-2,3-di hydro-1H-benzoimidazol-4-yloxy)-propyl]-acetamide as a white solid (86.0%), mp 114–116° C.; MS (+)FAB m/e 394 (M+H$^+$).

Elemental analysis for $C_{19}H_{18}F_3N_3O_3$ Calc'd: C, 58.01; H, 4.61; N, 10.68. Found: C, 57.67; H, 4.37; N, 10.49.

5d 2,2,2-Trifluoro-N-naphthalen-1-ylmethyl-N-[2-(2-oxo-2,3-dihydro-1H-benzoimidazol-4-yloxy)-ethyl]-acetamide as a white solid (90.0%), mp 88–90° C.; MS EI m/e 429 (M$^+$).

Elemental analysis for $C_{22}H_{18}F_3N_3O_3$ Calc'd: C, 61.54; H, 4.23; N, 9.79. Found: C, 61.34; H, 4.25; N, 9.52.

5e N-(4-tert-Butyl-benzyl)-2,2,2-trifluoro-N-[2-(2-oxo-2,3-dihydro-1H-benzoimidazol-4-yloxy)-ethyl]-acetamide as a white solid (84.9%), mp 184–185° C.; MS EI m/e 435(M$^+$).

Elemental analysis for $C_{22}H_{24}F_3N_3O_3$ Calc'd: C, 60.68; H, 5.55; N, 9.65. Found: C, 60.59; H, 5.55; N, 9.66.

5f 2,2,2-Trifluoro-N-[2-(2-oxo-2,3-dihydro-1H-benzoimidazol-4-yloxy)-ethyl]-N-thiophen-2-ylmethyl-acetamide as a white solid (73.3%), mp 49–50° C.; MS EI m/e 385 (M+).

5 g N-(4-Chloro-benzyl)-2,2,2-trifluoro-N-[2-(2-oxo-2,3-dihydro-1H-benzoimidazol-4-yloxy)-ethyl]-acetamide as a white solid (56.7%), mp 190–192° C.; MS(+)FAB m/e 414/416(M+H+).

Elemental analysis for $C_{18}H_{15}ClF_3N_3O_3$ Calc'd: C, 52.25; H, 3.65; N, 10.16. Found: C, 52.28; H, 3.55; N, 10.20.

5h N-Benzyl-N-[2-(6-chloro-2-oxo-2,3-dihydro-H-benzoimidazol-4-yloxy)-ethyl]-2,2,2-trifluoro-acetamide as a white solid (60.0%), mp 171–173° C.; MS (+)APCI m/e 414.2/416.2 (M+H+).

Elemental analysis for $C_{18}H_{15}ClF_3N_3O_3$ Calc'd: C, 52.25; H, 3.65; N, 10.16. Found: C, 52.10; H, 3.56; N, 9.96.

5i N-[2-(6-Chloro-2-oxo-2,3-dihydro-1H-benzoimidazol-4-yloxy)-ethyl]-2,2,2-trifluoro-N-thiophen-2-ylmethyl-acetamide as a white solid (70.1%), mp 153–154° C.; MS EI m/e 419/421 (M+).

Elemental analysis for $C_{16}H_{13}ClF_3N_3O_3S$: Calc'd: C, 45.78; H, 3.12; N, 10.01. Found: C, 45.85; H, 3.02; N, 9.73.

5j N-[2-(6-Chloro-2-oxo-2,3-dihydro-1H-benzoimidazol-4-yloxy)-ethyl]-2,2,2-trifluoro-N-thiophen-3-ylmethyl-acetamide as a white solid (77.8%), mp 152–153° C.; MS EI m/e 419/421 (M+).

Elemental analysis for $C_{16}H_{13}ClF_3N_3O_3S$: Calc'd: C, 45.78; H, 3.12; N, 10.01. Found: C, 45.86; H, 2.93; N, 9.76.

Intermediate 6

N-[2-(2{2,2,2-Trifluoroacetamidyl}-3-nitro-phenoxy)-ethyl]-N-benzyl-2,2,2-trifluoro-acetamide To a suspension of N-[2-(2-amino-3-nitro-phenoxy)-ethyl]-N-benzyl-2,2,2-trifluoro-acetamide (4.95 g, 12.9 mmol) in anhydrous methylene chloride (50 mL) at room temperature was added trifluoroacetic anhydride (3.18 g, 15.1 mmol). After 15 min the reaction was diluted with ether and washed with saturated sodium bicarbonate (3×80 mL) and the organic layer dried over anhydrous magnesium sulfate. Upon filtration and evaporation of the solvent gave 5.84 g (94.4%) of yellowish white solid, mp 114–115° C.; MS FAB m/e 480 (M+H+).

Elemental analysis for $C_{19}H_{15}F_6N_3O_5$ Calc'd: C, 47.61; H, 3.15; N, 8.77. Found: C, 47.35; H, 2.94; N, 8.69.

Intermediate 7

N-[2-(1-Methyl-2-{2,2,2-Trifluoroacetamidyl}-3-nitro-phenoxy)-ethyl]-N-benzyl-2,2,2-trifluoro-acetamide A suspension of potassium carbonate (1.44 g, 10.4 mmol), N-[2-(2-{2,2,2-trifluoroacetamidyl}-3-nitro-phenoxy)-ethyl]-N-benzyl-2,2,2-trifluoro-acetamide (1.0 g, 2.09 mmol) and methyl iodide (2.96 g, 20.9 mmol, previously filtered through basic alumina) in anhydrous dimethylsulfoxide (11 mL) was allowed to stir at room temperature for 24 h. The reaction mixture was poured into methylene chloride (200 mL) and extracted with water (2×80 mL). The organic layer was dried over anhydrous magnesium sulfate, filtered, and the solvent removed under vacuum to afford a yellow thick oil. Purification by chromatography (30% ethyl acetate-hexanes) afforded 960 mg (93.3%) of a light yellow solid, mp 90–92.5° C.; MS m/e EI 493 (M+).

Elemental analysis for $C_{20}H_{17}F_6N_3O_5$ Calc'd: C, 48.70; H, 3.47; N, 8.57. Found: C, 48.50; H, 3.27; N, 8.39.

Intermediate 8

N-Benzyl-2-(2-methylamino-3-nitro-phenoxy)-ethylamine

A suspension of potassium carbonate (2.52 g, 18.2 mmol) and N-[2–1-methyl-(2-{2,2,2-trifluoroacetamidyl}-3-nitro-phenoxy)-ethyl]-N-benzyl-2,2,2-trifluoro-acetamide (900 mg, 1.82 mmol) in methanol-water (50 mL:3 mL) was heated to reflux for 2 h then the solvent was evaporated and the residue dissolved in methylene chloride (100 mL) and extracted with water (80 mL). The organic layer was dried over anhydrous magnesium sulfate, filtered, and the solvent removed under vacuum. The residue was further purified by passing through a short pad of silica to afford 505 mg (92.1%) of N-benzyl-2-(methylamino-3-nitro-phenoxy) ethylamine as a red oil; MS FAB m/e 302 (M+H+).

Intermediate 9

N-Benzyl-[2-(2-methylamino-3-nitro-phenoxy)-ethyl]-carbamic acid tert-butyl ester A solution of N-benzyl-2-(2-methylamino-3-nitro-phenoxy)-ethylamine (480 mg, 1.59 mmol) and di-tert-butyl dicarbonate (348 mg, 1.59 mmol) in anhydrous tetrahydrofuran (6 mL) was allowed to stir for 3 hr. The reaction mixture was poured into methylene chloride (80 mL) and washed with water (50 mL). The organic layer dried over anhydrous magnesium sulfate, filtered, and the solvent evaporated to afford 593 mg (93%) of an orange solid, mp 91–93° C.; MS m/e EI 401 (M+).

Elemental analysis for $C_{21}H_{27}N_3O_5$ Calc'd: C, 62.83; H, 6.78; N, 10.47. Found: C, 62.78; H, 6.53; N, 10.51.

Intermediate 10

N-Benzyl-[2-(2-methylamino-3-amino-phenoxy)-ethyl]-carbamic acid tert-butyl ester To a mixture of N-benzyl-[2-(2-methylamino-3-nitro-phenoxy)-ethyl]-carbamic acid tert-butyl ester (520 mg, 1.30 mmol) and 10% palladium on carbon (120 mg ) in ethanol (40 mL) at 50° C. was added a solution of hydrazine hydrate (1.3 g) in ethanol (10 mL). The reaction was allowed to stir for 3 hr then the catalyst filtered through celite and the solvent removed. Purification by chromatography (30% ethyl acetate-hexane) afforded 380 mg (78.9%) of a clear oil; MS EI m/e 371 (M+); IR (film) 3400,3350,1680 cm−1.

Intermediate 11

N-Benzyl-[2-(2-oxo-1,3-dihydro-benzoimidazol-4-yloxy)-ethyl]-carbamic acid tert-butyl ester A mixture of N-benzyl-[2-(2-methylamino-3-amino-phenoxy)-ethyl]-carbamic acid tert-butyl ester (330 mg, 0.89 mmol) and diimidazole carbonyl (577 mg, 3.56 mmol) in anhydrous tetrahydrofuran (30 mL) was stirred a room temperature for 0.5 h and then heated to reflux for 3 h. The reaction was poured into water and extracted with ethyl acetate (2×150 mL). The organic layer dried over anhydrous magnesium sulfate, filtered, and the solvent removed. Purification by chromatography (50% ethyl acetate-hexane) afforded 268 mg (75.8%) of a foam; MS FAB m/e 398 (M+H+); IR (KBr) 3420, 3250, 1690 (bs) cm−1.

Intermediate 12

3-[2-(3,4-Dihydro-1H-isoquinolin-2-yl)-ethoxy]-benzene-1,2-diamine

The general procedure used in intermediate 4 using 2-[2-(3,4-dihydro-1H-isoquinolin-2-yl)-ethoxy]-6-nitrophenylamine (2k) afforded 3-[2-(3,4-dihydro-1H-isoquinolin-2-yl)-ethoxy]-benzene-1,2-diamine as a solid (95%), mp 76–77° C. This material was characterized as the dihydrochloride 0.4 H$_2$O salt; MS EI m/e 283 (M$^+$).

Elemental analysis for C$_{17}$H$_{21}$N$_3$O.2 HCl.0.4 H$_2$O: Calc'd: C, 56.17; H, 6.60; N, 11.56. Found: C, 56.15; H, 6.68; N, 11.25.

Intermediate 13

4-Chloro-2-(2-chloro-ethoxy)-6-nitro-phenylamine

A solution of 2-(2chloro-ethoxy)-6nitro-phenylamine (1a, 30.0 g, 0.14 mol), N-chlorosuccinamide and acetonitrile (1.3 L) was refluxed for 4 hr. The mixture was concentrated under vacuum and the residue was diluted with ethyl acetate (500 mL). The organic layer was washed with water (2×, 250 mL) and brine (250 mL), dried over anhydrous magnesium sulfate, filtered, and the solvent removed under vacuum to give an orange solid residue. Crystallization from ethyl acetate-hexane gave 33.5 g (95.3%) as orange solid, mp 109–110° C.; MS EI m/e 250/252/254 (M$^+$).

Elemental analysis for C$_8$H$_8$Cl$_2$N$_2$O$_3$: Calc'd: C, 38.27; H, 3.21; N, 11.16. Found: C, 38.15; H, 3.10; N, 10.96.

EXAMPLE 1

4-(2-Benzylamino-ethoxy)-1,3-dihydro-benzoimidazol-2-one

A suspension of potassium carbonate (1.15 g, 8.34 mmol) and N-benzyl-2,2,2-trifluoro-N-[2-(2-oxo-1,3-dihydro-1H-benzoimidazol-4-yloxy)-ethyl]-acetamide (0.38 g, 1.00 mmol) in methanol-water (30 mL:2 mL) was heated to reflux for 2 hr then the solvent was evaporated and the residue dissolved in ethyl acetate (100 mL) and extracted with water (80 mL). The organic layer was dried over anhydrous magnesium sulfate, filtered, and the solvent removed under vacuum to give the tide compound as a white solid, mp 132–135° C. Without further purification, this material was dissolved in ethyl acetate methanol (1:1) and treated with an excess amount of 1 N HCl in ether to afford 0.30 g (75.0%) of the hydrochloride salt as a light tan-colored solid, mp 230–233° C.: MS EI m/e 283 (M$^+$).

Elemental analysis for C$_{16}$H$_{17}$N$_3$O$_2$.HCl Calc'd: C, 60.09; H, 5.67; N, 13.14. Found: C, 59.84; H, 5.59; N, 12.92.

EXAMPLE 2

4-[2-(4-Methyl-benzylamino)-ethoxy]-1,3-dihydro-benzoimidazol-2-one

Following the general procedure used in example 1 and utilizing 2,2,2-trifluoro-N-(4-methyl-benzyl)-N-[2-(2-oxo-2,3dihydro-1H-benzoimidazol-4-yloxy)-ethyl]-acetamide·0.1 ethyl acetate (5b) afforded the title compound as a white solid (64.5%), mp 162–163 ° C.; MS (+)FAB m/e 298 (M+H$^+$). Treatment of the free base with ethereal HCl gave a white solid (90.0%), mp 244–246° C.: MS (+)FAB m/e 298 (M+H$^+$).

Elemental analysis for C$_{17}$H$_{19}$N$_3$O$_2$.1.0 HCl.1.7 H$_2$O Calc'd: C, 56.17; H, 6.46; N, 11.56. Found: C, 55.94; H, 6.05; N, 11.42.

EXAMPLE 3

4(7)-(2-Benzylamino-ethoxy)-1-(3)-methyl-1,3-dihydro-benzoimidazol-2-one

To a solution of N-benzyl-[2-(2-oxo-1,3-dihydro-benzoimidazol-4-yloxy)-ethyl]-carbamic acid tert-butyl ester in anhydrous methylene chloride (7 mL) was added trifluoroacetic acid (3 mL). After 15 min the reaction was poured into aqueous saturated sodium bicarbonate (150 mL) and extracted with methylene chloride (2×150 mL). The organic layer dried and the solvent removed to afford 170 mg (87%) a white solid: mp 137–138° C.; MS FAB 298 (M+H$^+$). The fumarate salt was prepared by adding a solution of the free base (165 mg) in warm isopropanol (15 mL) to an excess of fumaric acid in warm isopropanol (20 mL). Upon completion of addition crystals began forming and the mixture was allowed to cool to room temperature and the crystals filtered to afford 203 mg of fumarate salt, mp 201.5–202.5° C.; MS ESI m/e 298 (M+H$^+$).

Elemental analysis for C$_{17}$H$_{19}$N$_3$O$_2$.C$_4$H$_4$O$_4$ Calc'd: C, 61.01; H, 5.61; N, 10.16. Found: C, 60.73; H, 5.36; N, 9.95.

EXAMPLE 4

4-(3-Benzylamino-propoxy)-1,3-dihydro-benzoimidazol-2-one

Following the general procedure used in example 1 and using N-benzyl-2,2,2-trifluoroN-[3-(2-oxo-2,3-dihydro-1H-benzoimidazol-4-yloxy)-propyl]-acetamide (5c) afforded the title compound as a light yellow solid foam (90.4%); MS EI m/e 297 (M$^+$). Treatment of the free base with ethereal HCl gave the hydrochloride salt as a white solid (63.9%), mp 243–244° C.: MS EI m/e 297 (M$^+$).

Elemental analysis for C$_{17}$H$_{19}$N$_3$O$_2$.HCl: Calc'd: C, 61.17; H, 6.04; N, 12.59. Found: C, 60.92; H, 5.95; N, 12.41.

EXAMPLE 5

4-{2-[(Naphthalen-1-ylmethyl)-amino]-ethoxy}-1,3-dihydro-benzoimidazol-2-one

Following the general procedure used in example 1 and using 2,2,2-trifluoro-N-naphthalen-1-ylmethyl-N-[2-(2-oxo-2,3-dihydro-1H-benzoimidazol-4yloxy)-ethyl]-acetamide (5d) gave the title compound as a white solid (67.4%); MS EI m/e 333 (M$^+$).

Elemental analysis for C$_{20}$H$_{19}$N$_3$O$_2$: Calc'd: C, 72.05; H, 5.74; N, 12.60. Found: C, 71.72; H, 5.76; N, 12.22.
Treatment of the free base with ethereal HCl gave the quarter hydrate of the HCl as a white solid (63.9%), mp 223–225° C.: MS EI m/e 333 (M$^+$).

Elemental analysis for C$_{17}$H$_{19}$N$_3$O$_2$.HCl.quarter hydrate: Calc'd: C, 64.17; H, 5.52; N, 11.23. Found: C, 64.33; H, 5.42; N, 11.28.

EXAMPLE 6

4-[2-(4-tert-Butyl-benzylamino)-ethoxy]-1,3-dihydro-benzoimidazol-2-one

Following the general procedure used in example 1 and using N-(4-tert-butyl-benzyl)-2,2,2-trifluoro-N-[2-(2-oxo-2,3-dihydro-1H-benzoimidazol-4-yloxy)-ethyl]-acetamide (5e) gave the title as a white solid (84.5%); MS EI m/e 339 (M$^+$).

Elemental analysis for C$_{20}$H$_{25}$N$_3$O$_2$: Calc'd: C, 70.77; H, 7.42; N, 12.38. Found: C, 70.59; H, 7.44; N, 12.28.
Treatment of the tide compound with ethereal HCl gave the hemihydrated HCl salt as a white solid, mp 224–226° C.: MS EI m/e 339 (M$^+$).

Elemental analysis for C$_{20}$H$_{25}$N$_3$O$_2$.HCl.hemihydrate: Calc'd: C, 62.41; H, 7.07; N, 10.92. Found: C, 62.64; H, 6.93; N, 10.88.

EXAMPLE 7

4-{2-[(Thiophen-2-ylmethyl)-amino]-ethoxy}-1,3-dihydro-benzoimidazol-2-one

Following the general procedure used in example 1 and using 2,2,2-trifluoro-N-[2-(2oxo-2,3-dihydro-1H-benzoimidazol-4yloxy)-ethyl]-N-thiophen-2-ylmethyl-acetamide (5f), the title compound is obtained as a white solid (76.8%); MS EI m/e 289 (M$^+$).

Elemental analysis for $C_{14}H_{15}N_3O_2S$: Calc'd: C, 56.36; H, 5.41; N, 14.08. Found: C, 56.42; H, 5.04; N, 14.21. Conversion of the free base to the HCl salt with ethereal gave a white solid, mp 240–241° C.: MS EI m/e 289 (M$^+$).

Elemental analysis for $C_{14}H_{15}N_3O_2S$·HCl: Calc'd: C, 51.61; H, 4.95; N, 12.90. Found: C, 51.22; H, 4.82; N, 12.70.

EXAMPLE 8

4-[2-(4-Chloro-benzylamino)-ethoxy]-1,3-dihydro-benzoimidazol-2-one

Following the general procedure used in example 1 and using N-(4-chloro-benzyl)-2,2,2-trifluoro-N-[2-(2-oxo-2,3-dihydro-1H-benzoimidazol-4-yloxy)-ethyl]-acetamide (5g), the tide compound is obtained as a white solid (77.6%), mp 163–164° C.; MS (+)FAB m/e 318/320 (M+H$^+$).

Elemental analysis for $C_{16}H_{16}ClN_3O_2$: Calc'd: C, 60.48; H, 5.08; N, 13.22. Found: C, 60.17; H, 4.83; N, 13.20. Treatment of the free base with ethereal HCl yields the hydrochloride as a white solid, mp>250° C.: MS EI m/e 3171319(M$^+$).

Elemental analysis for $C_{16}H_{16}ClN_3O_2$·HCl: Calc'd: C, 54.25; H, 4.84; N, 11.86. Found: C, 54.18; H, 4.76; N, 11.87.

EXAMPLE 9

4-(2-Benzylamino-ethoxy)-6-chloro-1,3-dihydro-benzoimidazol-2-one

Following the general procedure used in example 1 and using N-(4-chloro-benzyl)-2,2,2-trifluoroN-[2-(6-chloro-2-oxo-2,3-dihydro-1H-benzoimidazol-4-yloxy)-ethyl]-acetamide (5h) afforded the tide compound as a white solid (77.6%), mp 192–193° C.; MS El m/e 3171319 (M$^+$).

Elemental analysis for $C_{16}H_{16}ClN_3O_2$: Calc'd: C, 60.48; H, 5.08; N, 13.22. Found: C, 60.24; H, 5.01; N, 13.09. Treatment of the free base with ethereal HCl gave the hydrochloride salt as a white solid, mp>250° C.: MS EI m/e 317/319 (M$^+$).

Elemental analysis for $C_{16}H_{16}ClN_3O_2$·HCl: Calc'd: C, 54.25; H, 4.84; N, 11.86. Found: C, 54.23; H, 4.85; N, 11.69.

EXAMPLE 10

6-Chloro-4-{2-[(thiophen-2-ylmethyl)-amino]-ethoxy}-1,3-dihydro-benzoimidazol-2-one Following the general procedure used in example 1 and using N-[2-(6-chloro-2-oxo-2,3-dihydro-1H-benzoimidazol-4-yloxy)-ethyl]-2,2,2-trifluoro-N-thiophen-2-ylmethyl-acetamide (5i) afforded the title compound as a white solid (89.0%), mp 179–180° C.; MS EI m/e 323/325 (M$^+$).

Elemental analysis for $C_{14}H_{14}ClN_3O_2S$: Calc'd: C, 51.93; H, 4.36; N, 12.98. Found: C, 51.80; H, 4.23; N, 12.96. Treatment of the title compound with ethereal HCl gave the hydrochloride as a white solid(90.0%), mp>250° C.: MS EI m/e 323/325 (M$^+$).

Elemental analysis for $C_{14}H_{14}ClN_3O_2S$·HCl: Calc'd: C, 46.68; H, 4.20; N, 11.66. Found: C, 46.52; H, 4.00; N, 11.57.

EXAMPLE 11

6-Chloro-4-{2-[(thiophen-3-ylmethyl)-amino]-ethoxy}-1,3-dihydro-benzoimidazol-2-one Following the general procedure used in example 1 and using N-[2-(6-chloro-2-oxo-2,3-dihydro-1H-benzoimidazol-4-yloxy)-ethyl]-2,2,2-trifluoro-N-thiophen-3-ylmethyl-acetamide (5j), the title compound is obtained as a white solid (89.0%), mp 182–183° C.; MS (+)FAB m/e 324/326 (M+H$^+$).

Elemental analysis for $C_{14}H_{14}ClN_3O_2S$: Calc'd: C, 51.93; H, 4.36; N, 12.98. Found: C, 51.96; H, 4.30; N, 12.95. The tide compound was treated with ethereal HCl to obtain the hydrochloride salt as a white solid (90.0% ), mp>250° C.: MS EI m/e 323/325 (M$^+$).

Elemental analysis for $C_{14}H_{14}ClN_3O_2S$·HCl: Calc'd: C, 46.68; H, 4.20; N, 11.66. Found: C, 46.29; H, 4.09; N, 11.51.

EXAMPLE 12

4-[2-(2,3-Dihydro-1H-isoquinolin-2yl)-ethoxy]-1,3-dihydro-benzoimidazol-2-one

Following the general procedure used in example 1 and using 2-[2-(3,4-dihydro-1H-isoquinolin-2-yl)-ethoxy]-6-nitro-phenylamine (2k) afforded the title compound as a white solid (63.0%), mp 173–174° C.; MS EI m/e 309 (M$^+$).

Elemental analysis for $C_{18}H_{19}N_3O_2$: Calc'd: C, 69.88; H, 6.19; N, 13.58. Found: C, 69.48; H, 6.01; N, 13.55. Treatment of the free base with ethereal HCl gave a quarter hydrate of the hydrochloride salt as a white solid (90.0% ), mp>250° C.: MS EI m/e 323/325 (M$^+$).

Elemental analysis for $C_{18}H_{19}N_3O_2$·HCl·0.25 $H_2O$: Calc'd: C, 61.71; H, 5.90; N, 11.99. Found: C, 61.90; H, 5.88; N, 11.97.

EXAMPLE 13

4-[2-(3-Phenyl-propylamine)-ethoxy]-1,3-dihydro-benzoimidazol-2-one

Following the general procedures used in intermediates 4 and 5 and example 1, N-[2-(2-amino-3-nitro-phenoxy)-ethyl]-2,2,2-trifluoro-N-(3-phenyl-propyl)-acetamide (3k) afforded the title comound as a white solid; MS (+)FAB m/e 312 (M+H$^+$).

Elemental analysis for $C_{18}H_{21}N_3O_2$·0.5 $H_2O$: Calc'd: C, 67.48; H. 6.92; N, 13.12. Found: C, 67.81; H. 6.76; N, 13.51. Treatment of the free base with ethereal HCl gave the hydrochloride salt as a white solid (90.9%), mp 243–245° C.; MS (+)FAB m/e 312 (M+H$^+$).

Elemental analysis for $C_{18}H_{21}N_3O_2$·HCl: Calc'd: C, 62.15; H, 6.38; N, 12.08. Found: C, 62.06; H, 6.21; N, 11.97.

Pharmacology

A method for determining intrinsic activity at the dopamine D2 receptor was to recently reported [Lahti et al., Mol. Pharm., 42, 432–438, (1993)]. Intrinsic activity is predicted using the ratio of the "low-affinity agonist" (LowAg) state of the receptor and the "high-affinity agonist" (HighAg) state of the receptor, i.e. LowAg/HighAg. These ratios correlate with the agonist, partial agonist, and antagonist activities of a given compound, which activities characterize a compounds ability to elicit an antipsychotic effect.

Affinity for the dopamine autoreceptor was established by a modification of the standard experimental test procedure of Seemen and Schaus, European Journal of Pharmacology 203: 105–109, 1991, wherein homogenized rat striatal brain tissue is incubated with $^3$H-quinpirole (Quin.) and various concentrations of test compound, filtered and washed and counted in a Betaplate scintillation counter.

High affinity for the dopamine D-2 receptor was established by the standard experimental test procedure of Fields, et al., Brain Res., 136, 578 (1977) and Yamamura et al., eds., Neurotransmitter Receptor Binding, Raven Press, N.Y. (1978) wherein homogenized limbic brain tissue is incubated with $^3$H-spiroperidol (Spiper.) and various concentrations of test compound, filtered and washed and shaken with Hydrofluor scintillation cocktail (National Diagnostics) and counted in a Packard 460 CD scintillation counter.

The results of the tests with compounds representative of this invention are given in the immediately following table

| Example # | $IC_{50}$ (nM) $D_2$ Quin. | $IC_{50}$ (nM) $D_2$ Spiper | Ratio |
|---|---|---|---|
| 1 | 0.51 | 60.6 | 118 |
| 2 | 0.29 | 28.5 | 98 |
| 3 | 2.92 | 1346 | 461 |
| 4 | 125.8 | 5979 | 47.5 |
| 5 | 0.60 | 38.7 | 64.5 |
| 6 | 0.81 | 47.8 | 59 |
| 7 | 0.51 | 254.6 | 499.2 |
| 8 | 0.30 | 99.5 | 331.7 |
| 9 | 0.48 | 34.6 | 70.6 |
| 10 | 0.47 | 58.0 | 123.4 |
| 11 | 0.31 | 67.0 | 216.1 |
| 12 | 12.0 | 657.5 | 55 |
| 13 | 0.30 | 30.0 | 100.0 |

Pharmaceutical Composition

Compounds of this invention may be administered neat or with a pharmaceutical carrier to a patient in need thereof. The pharmaceutical carrier may be solid or liquid.

Applicable solid carriers can include one or more substances which may also act as flavoring agents, lubricants, solubilizers, suspending agents, fillers, glidants, compression aids, binders or tablet-disintegrating agents or an encapsulating material. In powders, the carrier is a finely divided solid which is in admixture with the finely divided active ingredient. In tablets, the active ingredient is mixed with a carrier having the necessary compression properties n suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carrier may be used in preparing solutions, suspensions, emulsions, syrups and elixirs. The active ingredient of this invention can be dissolved or suspended in a pharmaceutically acceptable liquid carrier such as water, an organic solvent, a mixture of both or pharmaceutically acceptable oils or fat The liquid carrier can contain other suitable pharmaceutical additives such a solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (particularly containing additives as above, e.g., cellulose derivatives, preferable sodium carboxymethyl cellulose solution), alcohols (including monohydric alcohols and polyhydric alcohols, e.g., glycols) and their derivatives, and oils (e.g., fractionated coconut oil and arachis oil). For parenteral administration the carrier can also be an oily ester such as ethyl oleate and isopropyl myristate. Sterile liquid carriers are used in sterile liquid form compositions for parenteral administration.

Liquid pharmaceutical compositions which are sterile solutions or suspensions can be utilized by, for example, intramuscular, intraperitoneal or subcutaneous injection. Sterile solutions can also be administered intravenously. Oral administration may be as either a liquid or a solid dosage form.

The compounds of this invention may be administered rectally in the form of a conventional suppository. For administration by intranasal or intrabronchial inhalation or insufflation, the compounds of this invention may be formulated into an aqueous or partially aqueous solution, which can then be utilized in the form of an aerosol. The compounds of this invention may also be administered transdermally through the use of a transdermal patch containing the active compound and a carrier that is inert to the active compound, is non-toxic to the skin, and allows delivery of the agent for systemic absorption into the blood stream via the skin. The carrier may take any number of forms such as creams and ointments, pastes, gels, and occlusive devices. The creams and ointments may be viscous liquid or semisolid emulsions of either the oil in water or water in oil type. Pastes comprised of absorptive powders dispersed in petroleum or hydrophilic petroleum containing the active ingredient may also be suitable. A variety of occlusive devices may be used to realease the active ingredient into the blood stream such as a semipermeable membrane covering a reservoir containing the active ingredient with or without a carrier, or a matrix containing the active ingredient. Other occlusive devices are known in the literature.

The dosage to be used in the treatment of a specific patient suffering a dopamine imbalance must be subjectively determined by the attending physician. The variables involved include the severity of the dysfunction, and the size, age, and response pattern of the patient.

Treatment will generally be initiated with small dosages less than the optimum dose of the compound. Thereafter the dosage is increased until the optimum effect under the circumstances is reached. Precise dosages for oral, parenteral, nasal, or intrabronchial administration will be determined by the administering physician based on experience with the individual subject treated and standerd madical principles.

Preferably the pharmaceutical composition is in unit dosage form, e.g., as tablets or capsules. In such form, the composition is sub-divided in unit dose containing appropriate quantities of the active ingredient; the unit dosage form can be packaged compositions, for example packed powders, vials, ampoules, prefilled syringes or sachets containing liquids. The unit dosage form can be, for example, a capsule or tablet itself, or it can be the appropriate number of any such compositions in package form.

What is claimed is:

1. A method of treating diseases in a mama which respond to treatment by administration of a dopamine $D_2$ agonist which comprises administration to a mammal in need thereof of a therapeutically effective amount of a compound according to the formula

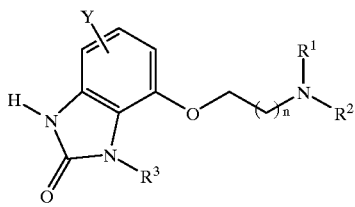

wherein:

$R^1$ is hydrogen or $C_1$–$C_6$ alkyl;

$R^2$ is selected from hydrogen, straight-chain and branched $C_1$–$C_{10}$ alkyl, cyclohexylmethyl or —$(CH_2)_m$Ar where Ar is phenyl, naphthyl, thienyl, furanyl or pyridinyl, each optionally substituted by one or two substituents selected independently from $C_1$–$C_6$ alkyl, halogen, $C_1$–$C_6$ alkoxide and trifluoromethyl;

or $NR^1R^2$ is 1, 2, 3, 4-tetrahydroquinolin-1-yl or 1, 2, 3, 4-tetrahydroisoquinolin-2-yl;

m is 1–5;

n is 1 or 2;

$R^3$ is hydrogen or $C_1$–$C_6$ alkyl;

Y is halogen, $C_1$–$C_6$ alkyl, and $C_1$–$C_6$ alkoxy;

or a pharmaceutically acceptable salt thereof.

2. The method of treatment according to claim 1 wherein the disease treated is schizophrenia.

3. The method of treatment according to claim 1 wherein the disease treated is Parkinson's disease.

4. The method of treatment according to claim 1 wherein the disease treated is Tourette's syndrome.

5. The method of treatment according to claim 1, wherein the disease treated is alcohol or drug addiction.

* * * * *